United States Patent
Kobayashi et al.

(10) Patent No.: US 6,789,899 B2
(45) Date of Patent: Sep. 14, 2004

(54) EYE'S OPTICAL CHARACTERISTIC MEASURING SYSTEM

(75) Inventors: Katsuhiko Kobayashi, Tokyo-to (JP); Gaku Takeuchi, Tokyo-to (JP); Masahiro Shibutani, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 230 days.

(21) Appl. No.: 09/972,304

(22) Filed: Oct. 5, 2001

(65) Prior Publication Data

US 2002/0049387 A1 Apr. 25, 2002

(30) Foreign Application Priority Data

Oct. 10, 2000 (JP) ........................................ 2000-309530

(51) Int. Cl.[7] ............... A61B 3/10; A61B 6/00
(52) U.S. Cl. ...................................................... 351/221
(58) Field of Search ................................. 351/200, 205, 351/206, 211, 216, 221, 246; 600/476, 558

(56) References Cited

U.S. PATENT DOCUMENTS 5,751,396 A * 5/1998 Masuda et al. ............. 351/221
6,629,761 B1 * 10/2003 Hirohara et al. ............ 351/221

* cited by examiner

Primary Examiner—George Manuel
(74) Attorney, Agent, or Firm—Nields & Lemack

(57) ABSTRACT

The eye's optical characteristic measuring system of the present invention comprises a projection system 2 for projecting a primary index image on fundus of an eye under testing, a photodetection system 3 for forming a secondary index image on a photoelectric detector 21 from a reflection light beam of the primary index image, detection systems 26, 27 and 28 for measuring a light amount intensity distribution characteristic of the secondary index image based on a signal from the photoelectric detector, a correction optical system 12 arranged in an optical path shared in common with the photodetection system and the detection system and for focusing the primary index image on the fundus of the eye under testing in corrected condition according to ocular refractive characteristic of the eye under testing, and a light beam switching means 13 for switching over to a first condition to guide the reflection light beam including the scattering reflection light beam from the fundus of the eye under testing to the photoelectric detector and to a second condition to guide only the totally reflected light beam from the fundus of the eye under testing to the photoelectric detector, wherein the system is designed in such manner that light amount intensity distribution characteristics of the secondary index images formed respectively by two light beams selected by the light beam switching means can be measured based on signals from the photoelectric detector under the condition corrected by the correction optical system.

3 Claims, 4 Drawing Sheets

REFLECTION

SCATTERING

EYE'S OPTICAL CHARACTERISTIC MEASURING SYSTEM

BACKGROUND OF THE INVENTION

The present invention relates to an eye's optical characteristic measuring system for measuring an optical characteristic of an ocular optical system by determining a light amount intensity distribution of an index image, which is projected to a fundus of an eye under testing.

In the past, an eye's optical characteristic measuring system has been known. In this conventional type system, an index image such as a pinhole image is projected to a fundus of an eye under testing. The index image is formed on a photoelectric detector from the reflected light beam. Based on a light amount intensity distribution characteristic of the index image, an eye's optical characteristic of the ocular optical system of the eye under testing is measured.

In this conventional type eye's optical characteristic measuring system, a primary index image is formed on the fundus by a light beam passing through the ocular optical system from a cornea to the fundus. The reflected light beam from the primary index image passes through the ocular optical system again, and a secondary index image is formed on the photoelectric detector. Based on a signal from the photoelectric detector, the 2-dimensional light amount intensity distribution characteristic of the secondary index image is measured. From the result of the measurement, an optical characteristic (PSF) (e.g. a point image intensity distribution function) of the ocular optical system of the eye under testing is calculated. It is advantageous in that, based on this optical characteristic, the index image formed on the fundus of the eye under testing can be calculated and displayed as a simulation image.

All of the light beam projected to the fundus of the eye under testing are not necessarily reflected. A part of the light beam enters from the surface of the fundus into a superficial layer. Thus, scattering reflection (the so-called bleeding reflection) occurs.

The degree of deterioration of the image caused by the bleeding reflection (scattering reflection) at the fundus of the eye is expressed as the optical characteristic of the fundus. A system for quantitatively measuring the optical characteristic of the fundus has not been proposed so far.

Therefore, in the conventional type eye's optical characteristic measuring system, the secondary index image includs the influence of deterioration of the image caused by the scattering reflection at the fundus. When the scattering reflection is received at the photoelectric detector together with the reflected light beam, it is turned to a noise in the light amount intensity distribution of the secondary index image, and the accurate eye's optical characteristic of the ocular optical system cannot be obtained.

SUMMARY OF THE INVENTION

It is a first object of the present invention to provide an eye's optical characteristic measuring system, by which it is possible to measure an amount to indicate a condition of deterioration caused by the scattering reflection at the fundus of the eye under testing, i.e. for quantitatively measuring an optical characteristic of the fundus. It is a second object of the present invention to provide a system, which can calculate and display a simulation image at real time, which a subject person recognizes at any focusing position as desired, based on the optical characteristic of the fundus thus obtained and based on the light amount intensity distribution of the secondary index image on the photoelectric detector.

To attain the above objects, the eye's optical characteristic measuring system of the present invention comprises a projection system for projecting a primary index image on fundus of an eye under testing, a photodetection system for forming a secondary index image on a photoelectric detector from a reflection light beam of the primary index image, a detection system for measuring a light amount intensity distribution characteristic of the secondary index image based on a signal from the photoelectric detector, a correction optical system arranged in an optical path shared in common with the photodetection system and the detection system and for focusing the primary index image on the fundus of the eye under testing in correcting condition according to ocular refractive characteristic of the eye under testing, and a light beam switching means for switching over to a first condition to guide the reflection light beam including the scattering reflection light beam from the fundus of the eye under testing to the photoelectric detector and to a second condition to guide only the totally reflected light beam from the fundus of the eye under testing to the photoelectric detector, wherein the system is designed in such manner that light amount intensity distribution characteristics of the secondary index images formed respectively by two light beams selected by the light beam switching means can be measured based on signals from the photoelectric detector under the condition corrected by the correction optical system. Also, the present invention provides an eye's optical characteristic measuring system as described above, wherein there is provided an arithmetic unit for calculating optical characteristic of fundus of an eye from light amount intensity distribution characteristics of the two secondary index images. Further, the present invention provides an eye's optical characteristic measuring system as described above, wherein there is provided a simulation image calculating means for calculating a primary index image on the fundus as recognized by a subject person under testing from an optical characteristic of the fundus as calculated in advance and from a light amount intensity distribution characteristic of the secondary index image when a first photodetection condition is selected.

DETAILED DESCRIPTION OF THE INVENTION

Figure 1:
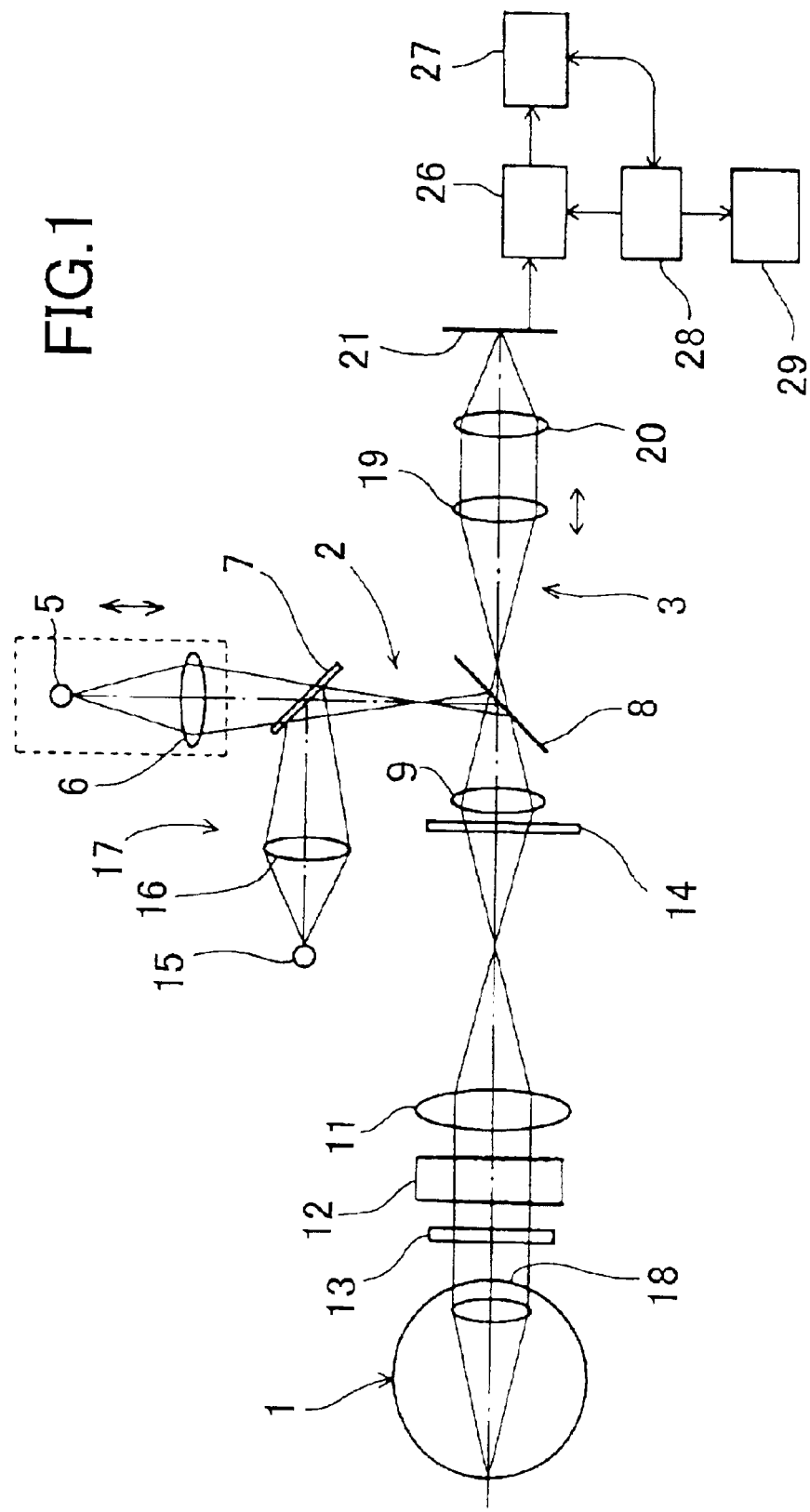
FIG. 1 is a schematical drawing of an optical system of an embodiment of the present invention.

Description will be given below on an embodiment of the present invention referring to the drawings.

Referring to FIG. 1, description will be given on an optical system of the embodiment of the present invention. In the figure, reference numeral 1 denotes an eye under testing, reference numeral 2 denotes a projection optical system, and reference numeral 3 denotes a photodetection optical system.

The projection optical system 2 comprises a light source 5, a projection lens 6 for converging a projected light beam emitted from the light source 5, a half-mirror 7 arranged on an optical axis of the projection lens 6, a polarization beam splitter 8 for reflecting a linearly polarized light component having a first polarization direction (S linearly polarized light) with respect to the projected light beam passing through the half-mirror 7 and for projecting toward the eye 1 under testing while for transmitting a P linearly polarized light having a direction of polarization deviated by 90° from that of the S linearly polarized light, a relay lens 9 disposed on an optical axis of a projection light beam of the polarization beam splitter 8 as arranged from the direction of the polarization beam splitter 8, an objective lens 11, a correction optical system 12 arranged between the objective lens 11 and the eye 1 under testing and comprising a spherical lens, a ¼ wave plate 13 disposed removably with respect to the optical axis, and an aperture diaphragm 14 arranged at a position approximately conjugate (including conjugate position) to a pupil 18 of the eye 1 under testing. Further, a fixed target system 17 comprising a fixed target 15 and a condenser lens 16 facing toward the half-mirror 7 is disposed. The light source 5 and the fixed target 15 are arranged at positions conjugate to the fundus of the eye 1 under testing. As to be described later, with respect to each of the light source 5 and the fixed target 15 images are formed on the fundus of the eye. The light source 5 and the projection lens 6 are integrally designed and can be moved together with a focusing lens 19 as described later along the direction of the optical axis.

In common with the projection optical system 2 the photodetection optical system 3 shares the polarization beam splitter 8, the relay lens 9 disposed on the projection light axis of the polarization beam splitter 8, the objective lens 11, the correction optical system 12, and the ¼ wave plate 13.

On the optical axis of the reflection light passing through the polarization beam splitter 8, there are provided the focusing lens 19, which can be moved along the optical axis of the reflection light, and an image forming lens 20. The image forming lens 20 forms an image from the reflected light beams on a photoelectric detector 21, which is disposed at a position conjugate to the fundus of the eye 1 under testing.

A photodetection signal from the photoelectric detector 21 is stored at a storage unit 27 via a signal processing unit 26. Writing of data from the signal processing unit 26 to the storage unit 27 is controlled by a control unit 28. Based on the data stored at the storage unit 27, the control unit 28 performs required calculations, and the result of the calculation is displayed on a display unit 29.

Figure 2A:
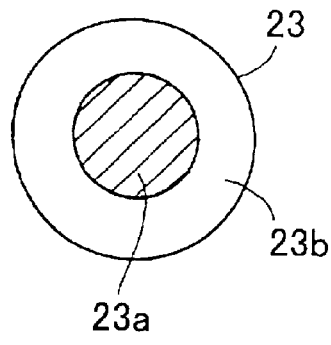
FIG. 2 represents drawings each showing an aperture diaphragm to be used in the above embodiment.
Figure 2B:
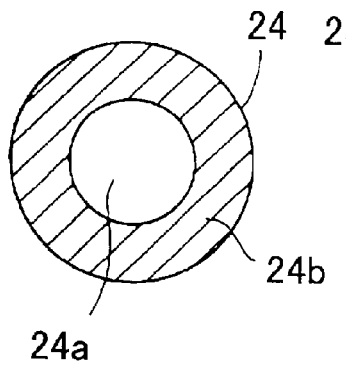

Description will be given on the aperture diaphragm 14 referring to FIG. 2(A), FIG. 2(B), and FIG. 2(C).

The aperture diaphragm 14 comprises three circular aperture plates 23, 24 and 25. The aperture plate 23 has a circular light shielding portion 23*a* at the center, and a peripheral annular portion serves as a transmitting portion 23*b*. The aperture plate 24 comprises a transmitting portion 24*a* in the same shape as the light shielding portion 23*a* and an annular light shielding portion 24*b* in the same shape as the transmitting portion 23*b*. In the aperture plate 25, two small fan-shaped portions are arranged at symmetrical positions, each having central angle of 45° as formed by dividing the circle in 8 equal parts, and these two small fan shaped portions serve as transmitting portions 25*a* and 25*a*. The remaining two large fan-shaped portions serve as light shielding portions 25*b* and 25*b*.

Figure 3:
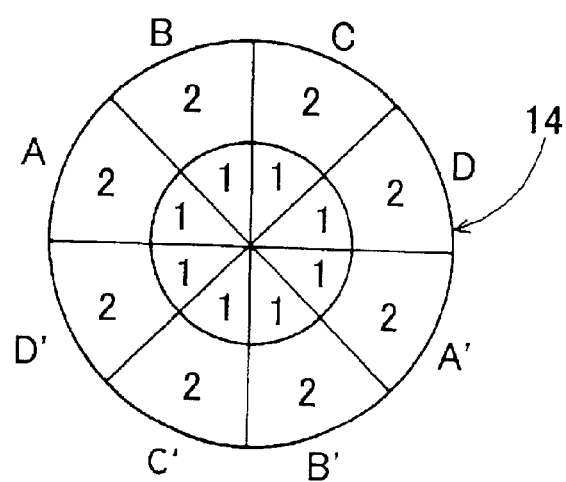
FIG. 3 is a drawing to explain status of regions divided by the aperture diaphragms.

By combining the aperture plates 23, 24 and 25 together, as shown in FIG. 3, apertures of A1, A2, B1, B2, C1, C2, D1 and D2, and also, apertures of A'1, A'2, B'1, B'2, C'1, C'2, D'1 and D'2 can be obtained.

Figure 2C:
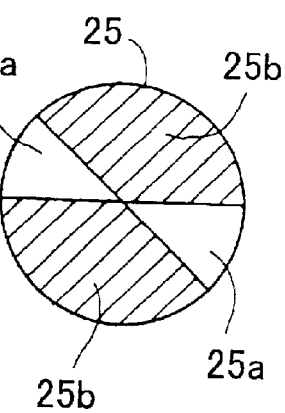

For instance, when the aperture plate 25 is set to the condition shown in FIG. 2(C) and the aperture plate 23 is combined with the aperture plate 25, the apertures A2 and A'2 can be obtained. When the aperture plate 24 is combined with the aperture plate 25, the apertures A1 and A'1 are obtained.

Further, when the aperture plate 25 is rotated step by step each time at an angle of 45° and is combined with the aperture plates 23 and 24 at each step, it is possible to obtain the apertures A1, A2, B1, B2, C1, C2, D1 and D2, and also, the apertures A'1, A'2, B'1, B'2, C'1, C'2, D'1 and D'2.

In the following, operation of the above optical system is described.

The focusing lens 19 is set to a reference position, the eye 1 under testing is instructed to gaze at the fixed target 15, and visual acuity of the eye 1 under testing is corrected by the correction optical system 12. The aperture diaphragm 14 is set to a position deviated from the optical axis.

After the correction of ocular refractive power, with the eye 1 under testing still gazing at the fixed target 15, the projection light beam is projected to the fundus of the eye under testing by the projection optical system 2. For the fixed target 15, a visible light is used, and an infrared light is used for the projection light beam.

First, description is given on a condition where the ¼ wave plate 13 is inserted to the optical path.

A projection light beam (infrared light) from the light source 5 passes through the projection lens 6 and the half-mirror 7 and reaches the polarization beam splitter 8. The S linearly polarized light component is reflected by the polarization beam splitter 8 and passes through the relay lens 9. Then, the light beam is projected to the fundus of the eye 1 under testing via the ¼ wave plate 13 by the objective lens 11 and the correction optical system 12, and a primary index image is formed on the fundus of the eye.

When the S linearly polarized light passes through the ¼ wave plate, it is turned to a right circularly polarized light. The projected light beam is totally reflected by the fundus of the eye 1 under testing. Being reflected by the fundus, the totally reflected light beam is turned to a left circularly polarized light. Further, when the totally reflected light beam passes through the ¼ wave plate 13, it is turned to the P linearly polarized light, which has a direction of polarization deviated by 90° from that of the S linearly polarized light.

The P linearly polarized light is guided toward the polarization beam splitter 8 by the correction optical system 12, the objective lens 11, and the relay lens 9. The polarization beam splitter 8 reflects the S linearly polarized light and allows the P linearly polarized light to pass. Thus, the totally reflected light beam passes through the polarization beam splitter 8. Then, the totally reflected light beam is formed as a secondary index image on the photoelectric detector 21 by the focusing lens 19 and the image forming lens 20.

Next, all of the projected light beam projected to the fundus of the eye 1 under testing are not necessarily reflected. A part of the light beam enters from the surface of the fundus into a superficial layer, and scattering reflection (the so-called bleeding reflection) occurs. When this scattering reflection light beam is received at the photoelectric detector 21 together with the totally reflected light beam, the scattering reflection light beam is turned to a noise in the light amount intensity distribution of the secondary index image, and the eye's optical characteristic of the ocular optical system cannot be measured.

The polarization status of the light beam under scattering reflection is in a random state. For this reason, when the light beam passes through the ¼ wave plate and is turned to the linearly polarized light, the light beam corresponding to the P linearly polarized light is limited to a part of the light components. Except the light corresponding to the P linearly polarized light out of the scattering light beam, all other light beam is reflected by the polarization beam splitter 8. Therefore, compared with the P linearly polarized light totally reflected by the fundus of the eye 1 under testing, the ratio of the P linearly polarized light due to the scattering reflection light beam is so slight as negligible.

Accordingly, the light which the photoelectric detector 21 receives is the totally reflected light beam, from which scattering reflection light component has been substantially removed. By using the ¼ wave plate 13 as a component element of the projection optical system 2 and the photodetection optical system 3, it is possible to measure accurate the eye's optical characteristic of the ocular optical system.

The light amount intensity distribution of the secondary index image received by the photoelectric detector 21 reflects the eye's optical characteristic of the eye 1 under testing itself. By detecting the photodetection status of the photoelectric detector 21, it is possible to measure the eye's optical characteristic.

Next, description will be given on a condition where the ¼ wave plate 13 is withdrawn from the optical path.

Because the ¼ wave plate 13 is removed, a polarizing status of the totally reflected light from the fundus remains to be the S linearly polarized light, and the totally reflected light is all reflected by the polarization beam splitter 8. Therefore, the light beam passing through the polarization beam splitter 8 is only the P linearly polarized light component of the scattering light beam reflected by the scattering reflection at the fundus. On the photoelectric detector 21, a secondary index image is formed by the scattering light beam. The light amount intensity distribution of the secondary index image received by the photoelectric detector 21 reflects the fundus optical characteristic and the eye's optical characteristic of the fundus and the eye 1 under testing.

Based on the photodetection status of the photoelectric detector 21 when the ¼ wave plate 13 is inserted, and also based on the photodetection status of the photoelectric detector 21 when the ¼ wave plate 13 is removed withdrawn, the fundus optical characteristic can be measured by the following procedure:

By inserting or removing the ¼ wave plate 13, it is possible to select whether the reflection light beam projected to the photoelectric detector 21 is the totally reflected light beam reflected by the fundus or the scattering reflection light beam reflected by the scattering reflection at the fundus of the eye. The ¼ wave plate 13 serves as a light beam switching means.

Figure 4A:
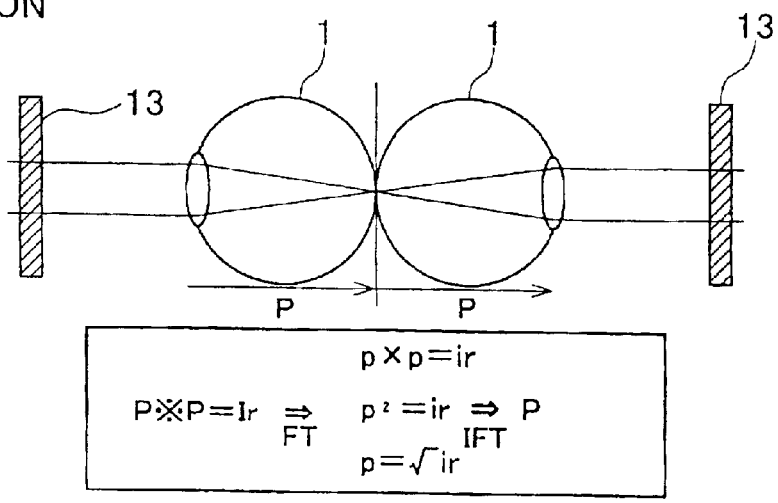
FIG. 4(A) is a drawing to explain a total reflection status at a fundus of an eye under testing.

First, as shown in FIG. 4(A), when the ¼ wave plate 13 is inserted to the optical path, i.e. when the scattering reflection light beam is removed, it is assumed that the optical characteristic of the optical system of the eye 1 under testing is P and also that a 2-dimensional light amount intensity distribution on the photoelectric detector 21 is Ir when the totally reflected light beam reflected by the fundus is received. Then, because the totally reflected light beam received at the photoelectric detector 21 passes through the eye 1 under testing twice, the following relationship exists between P and Ir:

$$P \otimes P = Ir$$

where the symbol $\otimes$ means convolution integration.

When Fourier transform is performed on P and Ir:

$$FT(P)=p, \text{ and } FT(Ir)=ir$$

Then, it is expressed as:

$$p^2 = ir \tag{1}$$

Figure 4B:
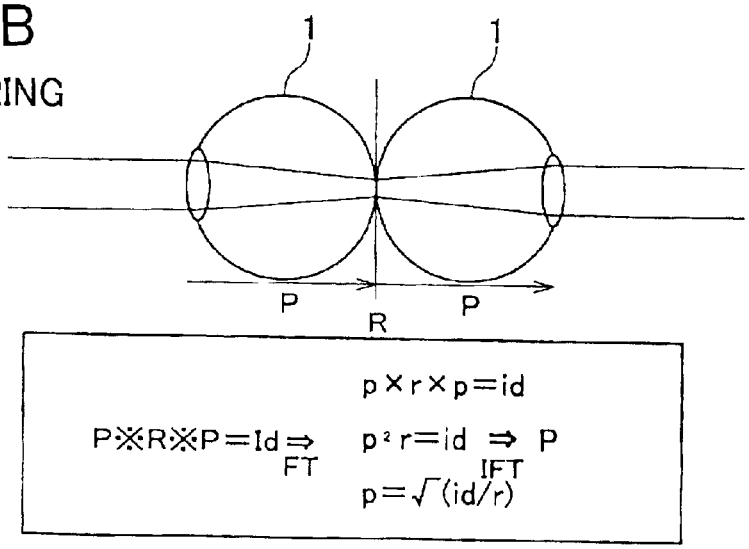
FIG. 4(B) is a drawing to explain a status of scattering reflection at the fundus of the eye under testing.

Next, as shown in FIG. 4(B), when the ¼ wave plate 13 is removed, i.e. when the reflection light beam comprises only the scattering reflection light, it is assumed that the optical characteristic of the ophthalmo-optical system of the eye 1 under testing is P. It is also assumed that optical characteristic of the fundus caused by the scattering reflection at the fundus is R, and a 2-dimensional light amount intensity distribution on the photoelectric detector 21 is Id when the scattering reflection light beam reflected by scattering reflection at the fundus is received. Then, the following relationship exists between P and Id because the scattering reflection light beam received at the photoelectric detector 21 passes through the eye 1 under testing twice and further the scattering reflection light beam is influenced by the optical characteristic of the fundus:

$$P \otimes R \otimes P = Id$$

When Fourier transform is performed on P, R and Id:

$$FT(R)=p, FT(R)=r, \text{ and } FT(Id)=id$$

Then, it is expressed as:

$$p \times r \times p = p^2 \times r = id \tag{2}$$

From the equations (1) and (2), $$r = id/ir$$

When inverse Fourier transform is performed, it is turned to:

$$R = IFT(id/ir) \tag{3}$$

That is, $$FT(Ir)=ir, \text{ and } FT(Id)=id \tag{4}$$

On the photoelectric detector 21, by measuring respectively the light amount intensity distribution Ir by the totally reflected light beam at the fundus and the light amount intensity distribution Id by the scattering light beam at the fundus, and based on the equation (3), it is possible to calculate an optical characteristic at the fundus, which quantitatively indicates deterioration of the image formed by the scattering reflection at the fundus.

By the procedure as described above, the optical characteristic of the fundus can be measured. By taking the optical characteristic at the fundus into account, it is possible to calculate a simulation image at the fundus.

By adjusting the correction optical system 12 or the focusing lens 19, the target image at the fundus when the target image is projected to the fundus of the eye under testing under any desired condition is simulated by the following procedure:

In this case, when light amount intensity of the index image formed on the photoelectric detector 21 is measured, the ¼ wave plate 13 is removed and the scattering light beam is received. There is no change in the optical characteristic of the fundus as obtained by the above procedure.

Here, it is supposed that an optical light transfer function of the eye optical system is Pa and an optical light transfer function of the fundus caused by the scattering reflection at the fundus is R, and also that the light amount intensity distribution on the photoelectric detector is Ia when the scattering reflection light beam is received. Then, $$Pa \otimes R \otimes Pa = Ia \quad (5)$$

Here, Fourier transform is performed as described above.

$$FT(Pa)=pa,\ FT(R)=r,\ \text{and}\ FT(Ia)=ia$$

Further, $$pa^2 \times r = ia$$

and $$pa = (ia/r) \quad (6)$$

Therefore, when inverse Fourier transform is performed:

$$Pa = IFT((ia/r)) \quad (7)$$

By measuring the light amount intensity distribution Ia on the photoelectric detector 21 and based on R calculated as described above, it is possible to calculate a light transfer function under any desired condition. By performing convolution integration on Pa thus calculated and also on the light amount intensity distribution function O of the target actually used, the simulation image of an image I projected on the fundus of the eye under testing can be calculated by the following equation:

$$I = Pa \otimes O \quad (8)$$

Therefore, by displaying the simulation image on the display unit, it is possible to observe an image at real time, which the subject person actually recognizes under any refractive power correction status and under any focusing status.

Figure 5:
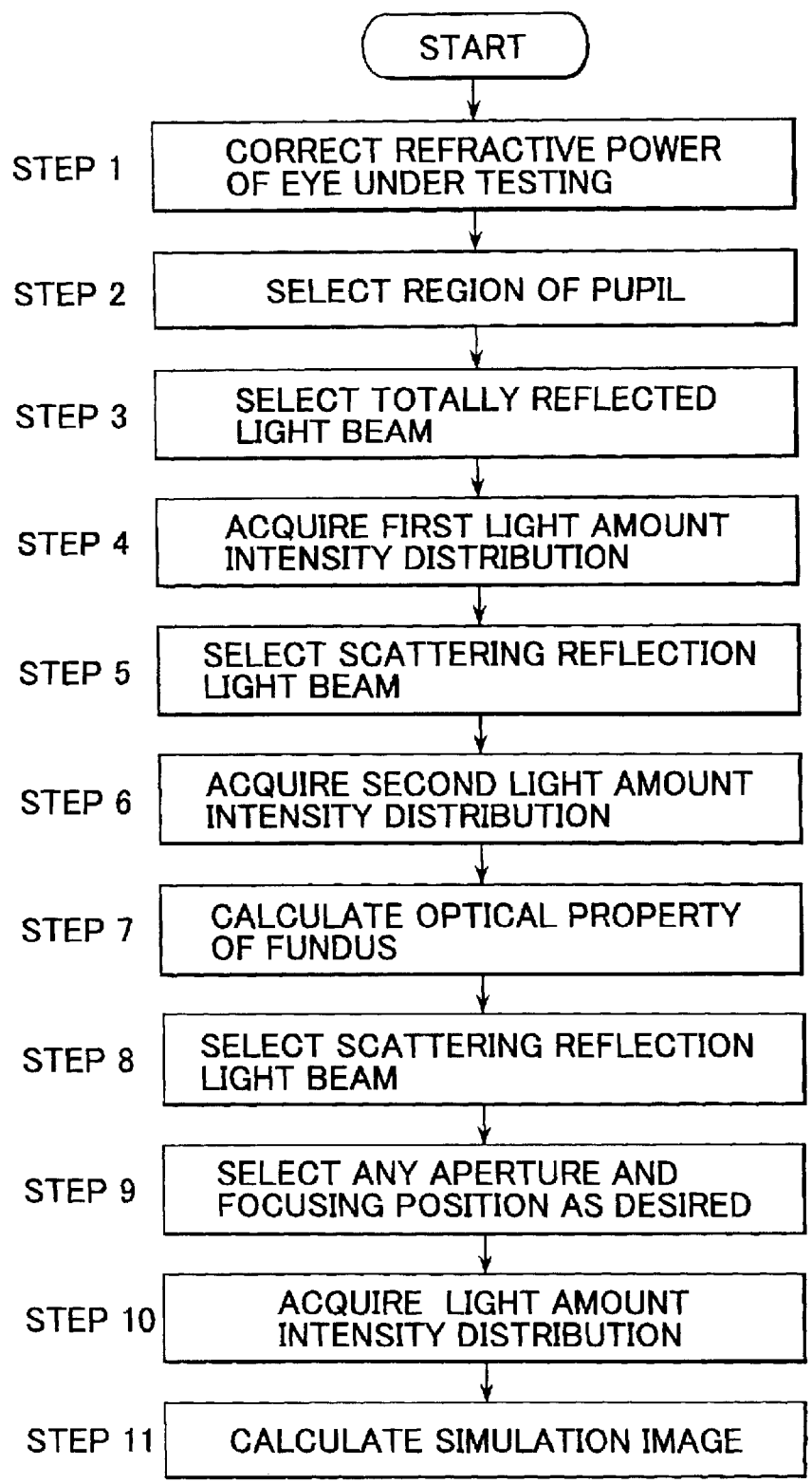
FIG. 5 is a flow chart of measurement procedures in the embodiment of the present invention.

Now, description will be given on the measurement of the eye's optical characteristic of the eye under testing referring to FIG. 5.

(Step 01) While the eye 1 under testing is instructed to gaze at the fixed target 15, visual acuity of the eye under testing is corrected according to spherical degree, astigmatic degree and astigmatic axis of the eye under testing by the correction optical system 12. For the correction, the following methods may be used: a method to perform correction based on the result of measurement of an objective refractometer measured in advance, or a method to observe the index image displayed on a monitor based on a signal from the photoelectric detector 21 and to perform correction so that the index image is observed as a point image.

(Step 02) The aperture diaphragm 14 is removed, or the aperture plate 24 is selected.

(Step 03) The ¼ wave plate is inserted, and the totally reflected light beam at the fundus is selected.

(Step 04) The secondary target image is formed on the photoelectric detector 21 by the totally reflected light beam, and a first light amount intensity distribution Ir is measured from a photodetection signal based on the secondary target image. The first light amount intensity distribution Ir is stored in the storage unit 27.

(Step 05) The ¼ wave plate 13 is removed, and the photodetection light beam is set to the reflected scattering light beam.

(Step 06) The secondary target image formed on the photoelectric detector 21 is formed only by the reflected scattering light beam. The second light amount intensity distribution Id is measured from the photodetection signal based on the secondary target image, and it is stored in the storage unit 27.

(Step 07) At the control unit 28, the optical characteristic R of the fundus of the eye 1 under testing is calculated from the result of measurements in Step 4 and Step 6. The fundus optical characteristic R is stored in the storage unit 27.

(Step 08) The ¼ wave plate 13 is removed, and the scattering reflection light beam is selected.

(Step 09) At the aperture diaphragm 14, an aperture as desired is selected. A focusing point as desired is selected by moving the focusing lens 19, or a correction status as desired is selected by the correction optical system 12.

(Step 10) From a photodetection signal based on the target image formed on the photoelectric detector 21, the light amount intensity distribution Ia is measured. The light amount intensity distribution Ia is stored in the storage unit 27.

(Step 11) Because the fundus optical characteristic R is already obtained, eye's optical characteristic Pa at any aperture and at any focusing state is obtained from the equations (5) and (7). Further, the simulation image is calculated by the equation (8). It is displayed on the display unit 29 or stored in the storage unit 27.

As explained in Step 11, the simulation image can be obtained at real time at any aperture of the aperture diaphragm 14. Therefore, by obtaining the simulation images under the conditions where the aperture plate 24 is inserted or the aperture plate 24 is removed, the images at the image at the fundus of the eye under testing can be seen under the conditions where an iris is enlarged or the iris is shrunk. In addition, this also applies to the simulation image under the limited condition such as the region B2 or region D1 in FIG. 3. Further, the image as recognized by the subject person can be seen at real time even in a process where ocular refractive power is being corrected.

According to the present invention, the eye's optical characteristic measuring system of the present invention comprises a projection system for projecting a primary index image on fundus of an eye under testing, a photodetection system for forming a secondary index image on a photoelectric detector from a reflection a light beam of the primary index image, a detection system for measuring a light amount intensity distribution characteristic of the secondary index image based on a signal from the photoelectric detector, a correction optical system arranged in an optical path shared in common with the photodetection system and the detection system and for focusing the primary index image on the fundus of the eye under testing in correcting condition according to ocular refractive characteristic of the eye under testing, and a light beam switching means for switching over to a first condition to guide the reflection light beam including the scattering reflection light beam from the fundus of the eye under testing to the photoelectric detector and to a second condition to guide only the totally reflected light beam from the fundus of the eye under testing to the photoelectric detector, wherein the system is designed in such manner that light amount intensity distribution characteristics of the secondary index images formed respectively by two light beams selected by the light beam switching means can be measured based on signals from the photoelectric detector under the condition corrected by the correction optical system. Thus, the condition of deterioration caused by the scattering reflection at the fundus of the eye under testing can be measured quantitatively. Further, the target image at the fundus as recognized by the subject person can be simulated and observed at real time because the condition of deterioration caused by the scattering reflection is measured quantitatively.

What is claimed is:

1. An eye's optical characteristic measuring system, comprising a projection system for projecting a primary index image on fundus of an eye under testing, a photodetection system for forming a secondary index image on a photoelectric detector from a reflection light beam of the primary index image, a detection system for measuring a light amount intensity distribution characteristic of the secondary index image based on a signal from the photoelectric detector, a correction optical system arranged in an optical path shared in common with the photodetection system and the detection system and for focusing the primary index image on the fundus of the eye under testing in correcting condition according to ocular refractive characteristic of the eye under testing, and a light beam switching means for switching over to a first condition to guide the reflection light beam including the scattering reflection light beam from the fundus of the eye under testing to the photoelectric detector and to a second condition to guide only the totally reflected light beam from the fundus of the eye under testing to the photoelectric detector, wherein the system is designed in such manner that light amount intensity distribution characteristics of the secondary index images formed respectively by two light beams selected by the light beam switching means can be measured based on signals from the photoelectric detector under the condition corrected by the correction optical system.

2. An eye's optical characteristic measuring system according to claim 1, wherein there is provided an arithmetic unit for calculating optical characteristic of fundus of an eye from light amount intensity distribution characteristics of said two secondary index images.

3. An eye's optical characteristic measuring system according to claim 2, wherein there is provided a simulation image calculating means for calculating a primary index image on the fundus as recognized by a subject person under testing from an optical characteristic of said fundus as calculated in advance and from a light amount intensity distribution characteristic of the secondary index image when a first photodetection condition is selected.

* * * * *